United States Patent [19]

Flax

[11] Patent Number: 5,560,242
[45] Date of Patent: Oct. 1, 1996

[54] ULTRASONIC SYSTEM EVALUATION PHANTOMS

[75] Inventor: Stephen W. Flax, Wauwatosa, Wis.

[73] Assignee: Flextech Systems, Inc., Brookfield, Wis.

[21] Appl. No.: 291,026

[22] Filed: Aug. 16, 1994

[51] Int. Cl.$^6$ .......................... G01N 37/00; G01N 29/06
[52] U.S. Cl. .......................................... 73/1 DV; 73/8664
[58] Field of Search .................... 73/1 DV, 1 R, 73/866.4, 865.6; 367/13; 434/268

[56] References Cited

U.S. PATENT DOCUMENTS

| | | | |
|---|---|---|---|
| 4,277,367 | 7/1981 | Madsen et al. | 252/408 |
| 4,286,455 | 9/1981 | Ophir et al. | 73/1 DV |
| 4,331,021 | 5/1982 | Lopez et al. | 73/1 DV |
| 4,463,592 | 8/1984 | Flax et al. | 73/1 DV |
| 4,470,303 | 9/1984 | O'Donnell | 73/602 |
| 4,476,549 | 10/1984 | Dragonette et al. | 73/1 DV X |
| 4,843,866 | 7/1989 | Madsen et al. | 73/1 DV |
| 4,903,523 | 2/1990 | Flynn | 73/1 DV |
| 4,974,461 | 12/1990 | Smith et al. | 73/1 DV X |
| 5,052,934 | 10/1991 | Carey et al. | 434/268 |
| 5,230,339 | 7/1993 | Charlebois | 73/1 DV X |
| 5,312,755 | 5/1994 | Madsen et al. | 436/8 |
| 5,341,808 | 8/1994 | Rickey et al. | 128/660.01 |

FOREIGN PATENT DOCUMENTS 1280534  12/1986  U.S.S.R. ................ 73/1 DV

OTHER PUBLICATIONS

"What a Hospital Physicist Needs in a Transducer Characterization Standard: Are Tissue Equivalent Test Objects Necessary"; *IEEE Transactions on Sonics and Ultrasonics*; vol. SU–26, No. 1; Jan. 1979 Paul R. Carson, pp. 1–6.

"Ultrasonic Phantom"; *Patent Abstracts of Japan* ABS Grp C1038, vol. 17, No. 142, ABS pub. date Mar. 23, 1993 (4–312452) inventor Shizuo Ishikawa.

Primary Examiner—Thomas P. Noland
Attorney, Agent, or Firm—Whyte Hirschboeck Dudek S.C.

[57] ABSTRACT

An ultrasound phantom and method of imaging are provided wherein the method quantifies data in decibels based on the log of a ratio of the signal intensity between adjacent regions within an ultrasound phantom. A phantom is disclosed for use with the method wherein the phantom can simulate the flow of blood within surrounding tissue. In one embodiment, the phantom is comprised of an open-cell, reticulated foam material matrix having a first density and at least one movable belt having a second density. The belt rotates on pulleys to simulate blood flow. The geometric relationship between the moving belt and the surrounding open-cell foam material provides a quantitative basis of assessing the beam forming characteristics of the imager as well as the ability of the system to separate the Doppler shifted signal from the stationary clutter signal. The belt can be provided with a shaped surface, such as scalloped, and the matrix can be biased against the surface so that rotation of the belt causes undulation at the surface interface between the belt and the matrix, thus simulating systaltic blood vessel movement. In another embodiment, the belt is replaced by a rotating disk of the same material as the belt such that differing blood flow rates between adjacent blood vessels can be simulated for ultrasonic imaging.

26 Claims, 6 Drawing Sheets

ULTRASONIC SYSTEM EVALUATION PHANTOMS

BACKGROUND OF THE INVENTION

1. Field of the Invention

This invention relates generally to the field of phantoms used in ultrasound evaluation to test the accuracy of and to calibrate ultrasonic equipment, and more particularly, to a method which can be used to quantitatively determine the imaging effectiveness of ultrasound devices at various depths and to a device which closely mimics the transmission pattern of ultrasonic waves propagating through one or more portions of the human body.

2. Description of the Prior Art

Although ultrasound equipment has been in use for a number of years, very few devices have been proposed which can be used to quantitatively assess the integrated performance level of the equipment, thus making it difficult to calibrate and check the equipment on a regular basis. This is especially true of diagnostic ultrasonic equipment used in the medical field. This type of diagnostic equipment should be calibrated using phantoms which are designed to mimic sound wave propagation characteristics of the human body. Ideally, such phantoms should be capable of approximating soft tissue with respect to (a) speed of sound, (b) attenuation coefficient, and (c) scattering coefficients. Additionally, such phantoms should also mimic other conditions which may be present at the investigation sight, such as blood flow or the systaltic movement of blood vessels.

A number of attempts have been made in the past to provide effective diagnostic ultrasound phantoms that mimic soft tissue. In a paper presented at the Second International Symposium on Ultrasonic Tissue Characterization in Gaithersburg, Md (1977), Eggleton describes work with soft plastics in the form of plastisols. At the same symposium, P.L. Carson, L. Shaboason and D.E. Dick presented a paper on work with polyurethane polymers. Also at the symposium, P. Edwards presented a paper describing work with gelatins.

More recently, U.S. Pat. No. 4,277,367, issued to Madsen et al., teaches a phantom which contains water-based pharmaceutical gelatins containing uniform distributions of various substances and known concentrations of alcohol. The substances act as scatterers within the gelatine matrix and may include solid particles of graphite, talc, pumice or polyethylene microspheres. Alternatively, the substances may include liquid particles of vegetable oil or kerosine. However, one drawback to this type of ultrasound phantom stems from the distribution of the scattering substance. Specifically, the scattering substances have a tendency to settle out of suspension, thus altering the ultrasound properties of the phantom. For example, when the gelatine is at temperatures over 90° F., suspended graphite begins to settle. Furthermore, it is often difficult to achieve and maintain a uniform dispersion of scattering substance throughout the gelatin. Also, many gelatins employed can be unstable under certain conditions, primarily due to bacterial attacks on the gel and ambient temperature variations, thus leading to degradation of the gelatin which can result in unpredictable operation.

Finally, it is often difficult to incorporate zones within the gelatin to mimic cysts or the like. Typically, a gelatine phantom is prepared by inserting a plug into uncongealed gelatin containing scattering material. Once the gelatin has hardened into a matrix, the plug is removed and gelatin containing no scattering material is allowed to congeal within the void. When scanned with an ultrasound system, waves should ideally pass unreflected through the plug in the same way they would pass through a cyst in the human body. One difficulty with this method, however, is the formation of an interface between the gel and the plug, resulting in an artifact. Specifically, a thin skin typically forms on the surface of the gelatin at the interface between the plug and the hardened gelatin matrix. During operation, this skin layer will cause a reflection resulting in the appearance of a ring down artifact within the cyst.

To overcome many of these problems, the use of open-cell reticulated foam material as the scatter matrix has been proposed. U.S. Pat. No. 4,286,455 issued to Ophir et al. teaches a phantom which includes a substantially air-tight enclosure having a quantity of reticulated synthetic resin foam material and a salt water solution therein. The ultrasonic characteristics of the phantom can be varied by using different foam materials and/or liquids. Further, localized zones having different ultrasonic qualities for mimicking various normal and pathological tissues can be provided by hollowed, cut-out regions, such as cylindrical cavities, within the foam material. Inserts with various scattering characteristics are provided within the hollowed regions. Ultrasonic waves directed through the phantom will be back-scattered by the fibers within the sponge while the forward wave will pass unscattered through the cut-out regions. If a plug has been inserted into the cut-out region, the echo of back-scattered waves from the plug will differ from that of the surrounding matrix.

However, even the reticulated foam type of phantom can only simulate imaging for static conditions within the human body. For phantoms which are intended to simulate dynamic conditions within the human body, such as blood flow or systaltic movement of vessels, other devices have been suggested. One method of simulating blood flow is through the use of a string phantom which generally utilizes a string riding between two pulleys in a water bath. As the pulleys rotate, the motion of the string is intended to appear as flowing blood when imaged with an ultrasound device. A disadvantage to this type of phantom is that scatter resulting from a string is not a realistic condition because the string acts as a "perfect" point target in a water bath. Thus the echo which is analyzed by the system is too ideal and does not indicate how the system will operate under more realistic conditions.

Another type of flow phantom utilizes fluid flow through tubes to simulate blood flow. A scatter material is mixed with fluid and then back-scatters sonic waves in much the same way as blood platelets reflect ultrasonic waves in blood. However, it is often difficult to maintain scatter particles in a uniform suspension to yield a constant scatter level. This is especially true at low flow rates because scatter particles tend to settle out of suspension. As scatter particles settle and become less uniformly distributed, it becomes difficult to mimic accurate flow rates over a wide range of flow velocities. Although pumping and stirring devices have been utilized to maintain uniform conditions, the devices are often expensive, greatly add to the complexity of the phantom and are only marginally effective.

Each of the above described phantoms can be used to approximate ultrasonic wave propagation through living tissue, allowing evaluation of ultrasound devices. This evaluation is based, in part, on the ultrasound system's ability to focus an ultrasonic beam. The ability to focus an ultrasonic beam, in part characterizes the imaging ability of the ultrasound system because those devices with better focusing ability produce higher quality images. The information provided by the phantom, however, goes beyond the evaluation of the beam forming characteristics of the system alone. That is, since the measurement is ultimately based upon the image formed by the total ultrasound system, the resulting quantitative measurement reveals the imaging characteristics of the total system. In this way, the measurement technique depicts the integrated response of the ultrasound system.

In an ideally focused ultrasound beam, energy is emitted and/or received in only the direction in which the beam is directed. That is, in the transmit mode, energy would only propagate out along an infinitely narrow line directed away from the transducer. Conversely, in the receive mode, the ultrasound system would only be sensitive to energy entering the transducer aperture from the direction in which the transducer is aimed. In other words, the transducer would be totally insensitive to any energy entering the aperture at an angle other than that at which the energy was emitted from the transducer. In effect, an ideal beam profile would appear to be a spacial impulse function directed in the steered beam direction.

In a non-ideally focused ultrasound beam, the beam profile will tend to converge and then diverge, as the beam propagates, resulting in a beam profile that has some finite width and is characterized by a central main lobe and weaker side lobes. The integral of the main lobe, which is represented by a first discreet amount of energy, and the integral of the side lobe energy, represented by a second discrete amount of energy, are both simultaneously detected by the transducer as a summation. To the extent that the main lobe of the ultrasound beam pattern is sufficiently narrow, then the main lobe can be considered as approximating a spacial impulse function. In this case, the signal energy contained in the beam side lobes can be considered as an unwanted signal or noise. An image formed under these conditions is the summation of the desired main lobe energy and the undesired side lobe "noise" energy. In the event that the main beam is broad, then energy falling beyond a specified spacial angle would also be considered noise even though it was technically part of the main lobe. The less focused the ultrasound beam, the greater the proportional amount of energy found outside the desired beam direction, and hence, the lower the signal to noise ratio.

It is readily recognized in the field of ultrasonic imaging that the width of the main lobe and the height of the side lobes of a beam formed by ultrasonic waves play a significant role in determining clinical image quality. It is known in the prior art that the energy level found in the side lobes of ultrasound beams increases with beam degradation. Generally, commercially available cyst phantoms are used to qualitatively evaluate how well an ultrasound beam can detect a cyst or sonolucent region within a phantom, i.e., how well the device can focus an ultrasonic beam at a given depth. Since no echo should be generated in cystic regions because of the absence of scatter material, any ultrasonic energy that does appear to be reflected from cystic regions is actually caused by side lobe insonification of the adjacent regions.

In other words, although ideally a transducer which propagates an ultrasonic beam through a cyst should not receive any signal because there is no scatter material in the region of the cyst, in reality the transducer will receive side lobe energy (or energy from the periphery of the main lobe) from regions adjacent to the straight path of the beam. The effect is that there does appear to be some back-scatter emanating from the region of the cyst. For example, on the display screen a true cyst at a predetermined depth should appear black because there should be no sonic reflection from the cyst. Because the ultrasound device is not capable of perfectly focusing an ultrasonic beam, the image of the cyst on the display screen will appear to have some level of echo, i.e., the cyst would have a salt and pepper appearance on the screen.

Thus, although an image may be generated by the ultrasonic scan of a phantom, it is often difficult to determine which portion of the image can be attributed to the desired signal from the steered direction and which part is due to off angle energy contained in either the side lobes or the edges of a broad main lobe. With only qualitative information about a device's imaging capabilities, it becomes difficult to conduct diagnostic system evaluations. Additionally, the lack of quantitative data makes it difficult to compare system performance.

Quantitative methods of ultrasound evaluation have been proposed utilizing a phantom with isolated regions of different scatter intensity within the matrix. In these procedures, an isolated region within a phantom is scanned with a first ultrasound device and the resulting image is compared to the image produced by a second ultrasound device. It has been suggested that the difference in the images is a quantitative means which can be interpreted to determine the imaging capabilities of the ultrasound devices in question. This method, however, produces only relative results because there is no absolute standard to which the information can be compared. Additionally, this method is subject to variables which are functions of the conditions surrounding each individual test, such that there are no standardized test conditions. Therefore, any information gleaned from the resulting ultrasound images may potentially be even further skewed by dissimilar test conditions. For example, the relative contrast difference between scatter regions is a function of the ultrasound system's gain, the signal center frequency, the signal band width, the spectral shape and the depth of the region within the phantom. Thus the results are only partially a function of the beam pattern and are also comprised of parameters which are not constant with each test.

Therefore, it is desirable to provide a method for quantifying ultrasonic image data such that the data is based only on the beam pattern and not on the conditions particular to each test. The quantified information should be in a form that is standardized to allow comparison with other ultrasound systems. Additionally, it would be desirable to provide a phantom which can simulate blood flow at various velocities and through different diameter vessels. Lastly, it would be desirable to provide a phantom which can simulate systaltic conditions within a living body.

SUMMARY OF THE INVENTION

The present invention provides a method which can be used to determine the imaging effectiveness of ultrasound devices at various depths by generating quantitative data which can be compared to a standard or absolute base. The method quantifies data in decibels based on the log of a ratio of the signal intensity between adjacent regions within a ultrasound phantom. Because the quantitative number produced is a ratio, signal variations within different test zones are proportionate and the effect of the conditions surrounding each test are nullified. Specifically, the method comprises: using the ultrasound device under investigation to generate a signal level calibration curve which plots image brightness as a function of the signal level (in decibels); imaging adjacent echogenic and sonolucent regions in an ultrasound phantom using the ultrasound device under investigation; averaging the brightness levels generated from adjacent echogenic and sonolucent regions within the phantom; and computing the relative difference between signal levels using the signal level calibration curve. This difference is a quantitative number that indicates the imaging capability of the ultrasound system under investigation, such that the larger the number, the better the imaging capability.

The invention further provides an ultrasound phantom for use with said method wherein the phantom can be used to characterize the ability of ultrasound systems to focus at various depths. In a preferred embodiment, this phantom has multiple regions which are characterized by an echogenic matrix and vertical, well-shaped sonolucent regions. The sonolucent regions are of the same shape and dimension and no sonolucent region shares the same axis. This insures that attenuation resulting from scatter does not produce an unwanted artifact in the region of interest.

Finally, the invention provides a phantom for use with said method wherein the phantom can simulate the flow of blood within the arteries, as well as the systaltic movement of the arteries. In one embodiment, the phantom is comprised of an open-cell, reticulated foam material matrix having a first density and at least one open-cell, reticulated foam material belt having a second density which is usually lower or finer than the first density. The belt rotates on pulleys to simulate blood flow. In another embodiment, the belt is provided with a shaped surface, such as scalloped, and the matrix is biased against the surface so that rotation of the belt causes undulation at the surface interface between the belt and the matrix. The effect when monitored by an ultrasound device is that of systaltic organ movement. In still yet another embodiment, the belt is replaced by a rotating disk comprised of the same material as the belt. Because the radial velocities of points along a radially extending line differ as the disk rotates, the device can mimic differing blood flow rates between adjacent blood vessels.

BRIEF DESCRIPTION OF THE DRAWINGS

In the drawings which illustrate that which is presently regarded as the best modes for carrying out the invention:

FIG. 5b is a sectional, front view of the phantom described in FIG. 5a.

FIG. 5c is a sectional, top view of the phantom described in FIG. 5a.

FIG. 7b is a sectional, side view of the rotating disk phantom shown in FIG. 7a.

DESCRIPTION OF THE PREFERRED EMBODIMENTS

Figure 1A:
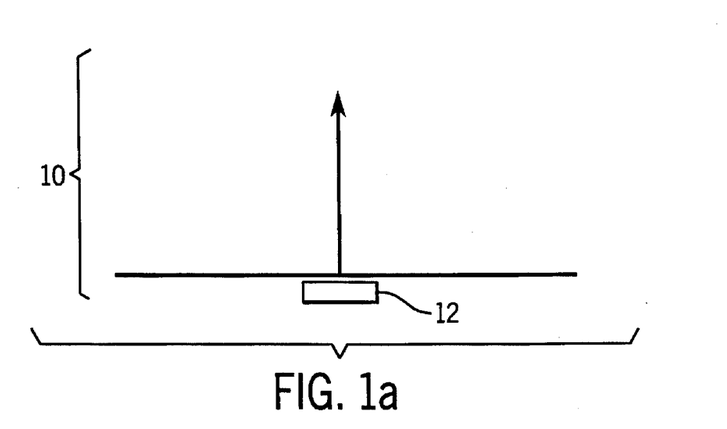
FIG. 1a illustrates an ideal ultrasonic beam profile imaging a round cyst in a phantom.
Figure 1B:
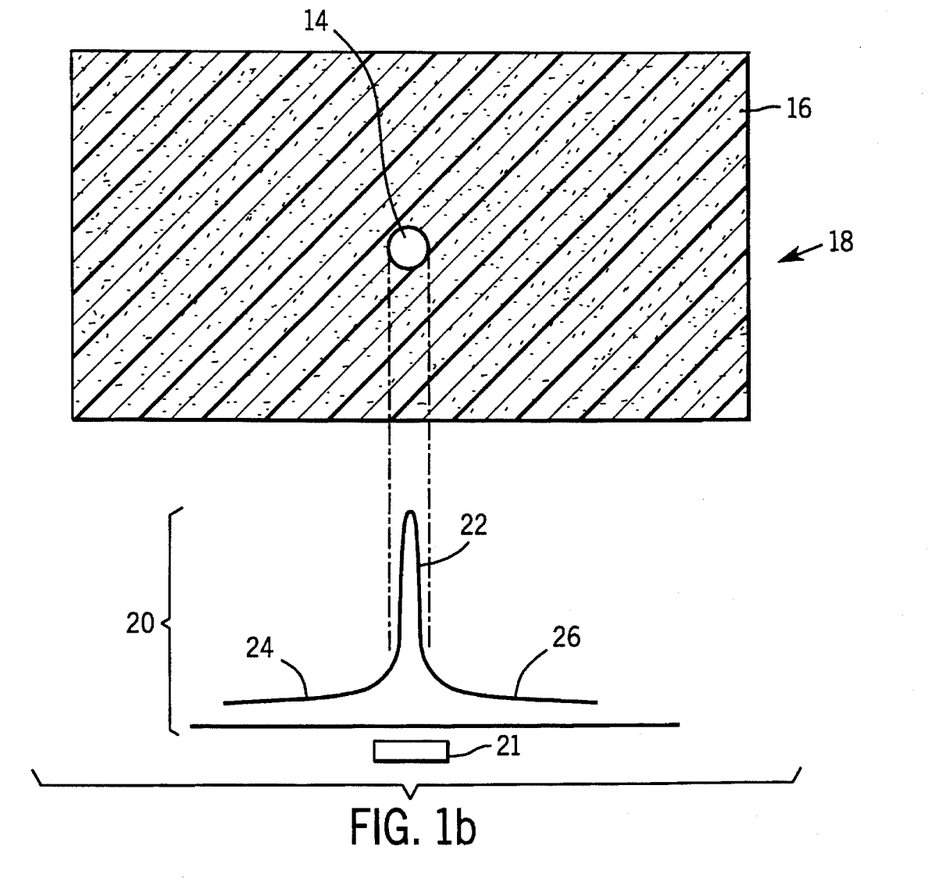
FIG. 1b illustrates a non-ideal ultrasonic beam profile imaging a round cyst in a phantom.

FIGS. 1a and 1b illustrate ultrasonic beam profiles imaging a cylindrical cyst. Specifically, FIG. 1a shows an ideally focused ultrasound beam 10, generated by an ideal ultrasound transducer 12, in which the energy of beam 10 is emitted and/or received in only the direction in which beam 10 is focused. Beam 10 is focused on a sonolucent region 14 which appears within an echogenic region 16 of a phantom 18. In the transmit mode, ideal ultrasound transducer 12 propagates energy only out along an infinitely narrow line directed away from transducer 12. Conversely, in the receive mode, ideal ultrasound transducer 12 is only sensitive to energy arriving at transducer 12 along the same propagation path in which the energy was transmitted. Ideal ultrasound transducer 12 is totally insensitive to any energy directed to it at an angle other than that at which ultrasonic energy was originally transmitted.

In FIG. 1b, a non-ideally focused beam profile 20 generated by a non-ideal ultrasound transducer 21 is shown. Beam profile 20 is characterized by a central main lobe 22 and side lobes 24, 26. Main lobe 22 represents a first discreet amount of energy and has a finite beam width. Side lobes 24, 26 each represent a second, discreet amount of energy. When the ultrasonic energy of the main lobe and side lobes is converted to electrical energy, the resulting signal can be displayed on a monitor, such that regions of high energy reflectance appear as bright areas on the monitor and regions of low energy reflectance appear as dark areas on the monitor. For a reasonably focused transducer, the energy in the main lobe should be confined to a narrow angular region and the main lobe energy should be much higher than that found in the side lobes. In such a case, if the ultrasound beam is aimed at a sonolucent region within the scatter phantom, then the main lobe of the beam would be centered in that sonolucent region. Those skilled in the art will understand that if a region contains no scatter material, then no energy shall be reflected back to the transducer from that region. Conversely, if a region contains a large amount of scatter material, then comparatively large amounts of ultrasonic energy will be reflected when imaged with an ultrasound system. As FIG. 1b further illustrates, the main lobe energy and the side lobe energy are both simultaneously detected by non-ideal ultrasound transducer 21 as a summation. Therefore, non-ideal ultrasound transducer 21 is sensitive to two types energy: first, the main lobe energy arriving at transducer 21 along the same propagation path in which the energy was originally transmitted; and second, off axis or side lobe energy, arriving along propagation paths other than the original main lobe energy propagation path.

The quality of an ultrasound system is based in part on the system's ability to focus ultrasound beams so that detection of side lobe energy is minimized. An ultrasound system's ability to focus a beam is comprised of the ability of the transducer to converge a beam at a focal point and the ability of the beam to image regions above and below the focal point.

The method of the present invention allows a quantitative assessment of an ultrasound system's ability to image regions above and below a focal point as well as at the focal point. In accordance with the method, a signal level calibration curve which plots image brightness as a function of signal level is generated using the ultrasound system under investigation. Next, the ultrasound system is used to image adjacent echogenic and echolucent regions in an ultrasound phantom. The brightness levels generated from the adjacent echogenic and echolucent regions are each separately averaged. Finally, the relative difference between signal levels is computed using the signal level calibration curve and the average brightness levels. This difference is a quantitative number that indicates the imaging capability of the ultrasound system under investigation. As will be further explained below, it has been found that the larger this quantitative number, the better the imaging capability of the ultrasound system.

Figure 2:
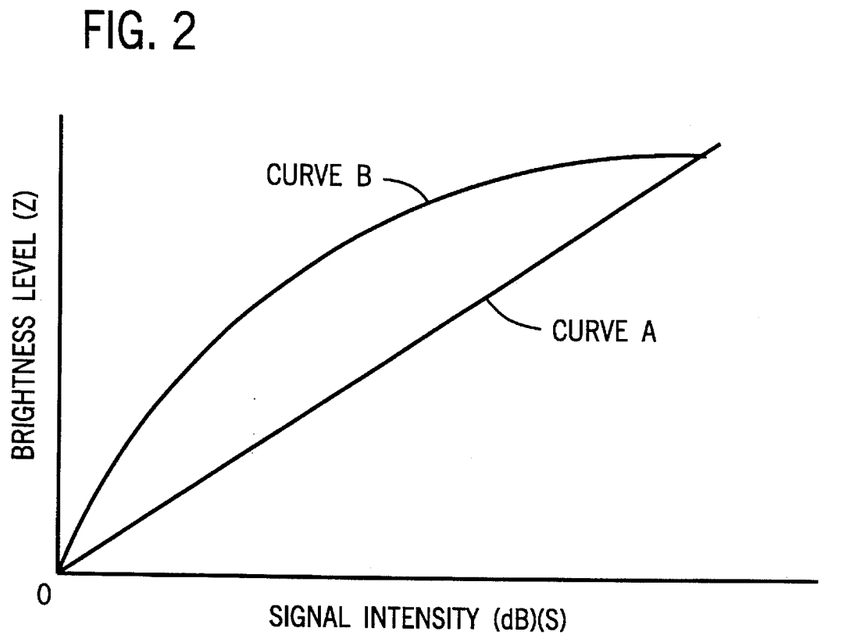
FIG. 2 is a signal level calibration curve which plots signal level against brightness.

More specifically, in the first step of the process an ultrasound system's gray level mapping pattern has to be calibrated to a measured decibel scale. This is accomplished by plotting signal levels (measured in decibels) along the x-axis, brightness levels along the y-axis and fitting a curve to the points on the graph. For each point on the graph, an ultrasonic signal is generated from a source, transmitted through a coupling media, and received by the ultrasound system under investigation, such that a brightness pattern is produced on the screen of the ultrasound system. This pattern is then recorded using a standard video frame grabber which is well known in the art and will not be described herein. Next, the transmitted ultrasound signal is altered by a known amount using a wide band precession attenuator and the above mentioned process is repeated for this second signal. For example, the second signal might be attenuated by precisely 10 dB's from the original signal. The result is a similar image to that produced using the original signal, however, the gray level brightness pattern observed will be reduced by some amount. This second pattern is again recorded using a video frame grabber. This process is repeated for as many signal levels as practical (usually 6 to 8) such that the observed grey level brightness pattern varies from nearly full white to nearly full black. The resulting brightness levels are then plotted as a function of the signals to which they correspond. This process yields a curve, illustrated in FIG. 2, that relates changes in the system's gray level display to changes in the signal level. Ideally the curve should be linear as illustrated by Curve A. However, some systems do not follow this ideal behavior and may exhibit performance more similar to that illustrated by Curve B. This calibration curve will be used in a subsequent step to determine a quantitative value which can be used to assess the ultrasound system's imaging capability.

In the second step of the process, a special ultrasound phantom is imaged using the ultrasound system under investigation. The special phantom consists of an echogenic region and at least one sonolucent region. The echogenic region contains uniform scattering material. Sonographically, the echogenic region will image on the monitor with a characteristic salt and pepper pattern well known in the field. Conversely, as explained above, a truly scatter free, i.e., sonolucent, region should produce no echoes and consequently that region should appear to be totally black. However, because the ultrasound system is not ideal, some signal energy, i.e., from the edges of the main lobe or the side lobe energy, resulting from the ultrasound beam insonifying scatter regions adjacent to the sonolucent region will appear to be coming from the sonolucent region. The image generated in this step can be recorded utilizing standard "screen grabbing" techniques which are well known in the art and will not be described herein.

The third step of the method is to compute the difference in scatter intensity between the sonolucent region and the adjacent echogenic region at the depth of interest. The third step is comprised of several sub-steps. First, a depth of interest within the special phantom is selected. The depth selected should contain both a sonolucent and an echogenic region. Second, two smaller regions of interest are defined at the depth of interest on the image that was grabbed in step two. The first region of interest is defined by an area within the sonolucent region. The second region of interest is defined by an area within the echogenic region such that the second region of interest is adjacent to the first region of interest. Third, the average brightness level within the first and second regions of interest is computed to yield a first brightness level, $Z_1$, and second brightness level, $Z_2$. This may be done by treating each region of interest as a two dimensional array and averaging the brightness level of the pixels within the array. Those skilled in the art will understand that the first brightness level, $Z_1$, will be less than the second brightness level, $Z_2$ because of the lack of scatter material in the sonolucent region. Fourth, each brightness level is found on the signal level calibration curve and a corresponding signal is determined, such that first brightness level, $Z_1$, will correlate to a first signal level $S_1$ and second brightness level, $Z_2$, will correlate to a second signal level $S_2$. Once first brightness level $Z_1$ and second brightness level $Z_2$ have been determined, the fifth step is the subtraction of first brightness level $Z_1$ from second brightness level $Z_2$ to yield a quantitative number which can be used to evaluate the imaging effectiveness of the ultrasound system.

As described above, both the corresponding brightness values, $Z_1$ and $Z_2$, are measured in decibels (dB). As such, they relate to the corresponding signal values $S_1$ and $S_2$, as $$Z_1 = 20*\log(S_1) \text{ and } Z_2 = 20\log(S_2).$$

Thus, calculating the brightness difference between the two regions is equivalent to subtracting the value of one region from the other. Hence, $$\text{Delta} = Z_1 - Z_2 = 20*(\log(S_1) - \log(S_2)).$$

This, in turn, is equivalent to taking the log of the ratio of $S_1$ and $S_2$. Hence, $$\text{Delta} = Z_1 - Z_2 = 20*(\log(S_1/S_2)).$$

In actuality, both the signal levels, $S_1$ and $S_2$, will be finite. For the worst case, if a scanner is unable to distinguish between the cystic region and the surrounding scatter region, then $S_1$ would equal $S_2$. For such a poor case, the signal level difference in decibels would be zero. As a scanner is better able to distinguish between the cystic region and the surrounding region, the ratio will increase, resulting in a larger Delta value. The larger the Delta value, the better the scanner is functioning at that particular measurement depth.

The method of this invention provides a quantitative value which is free from the influence of outside variables. For example, the gain, i.e., brightness, on most ultrasound monitors can be adjusted to the taste of the viewer. Therefore, any quantitative value based on the brightness of the image on the screen is subject to the gain setting for that particular ultrasound system. To generate a meaningful quantitative value which could be compared to quantitative values generated for other ultrasound systems, the gain on each monitor would need to be standardized. The method of the present invention, however, nullifies the effects of the gain settings because only the relative difference between the brightness levels is significant and not the actual brightness levels themselves.

The above described method, therefore, provides a quantitative value indicating, in decibels, how well the sonolucent and echogenic regions are delineated. The resulting value, in turn, represents the sum total of how well the ultrasound system is able to image an echolucent region.

Figure 3:
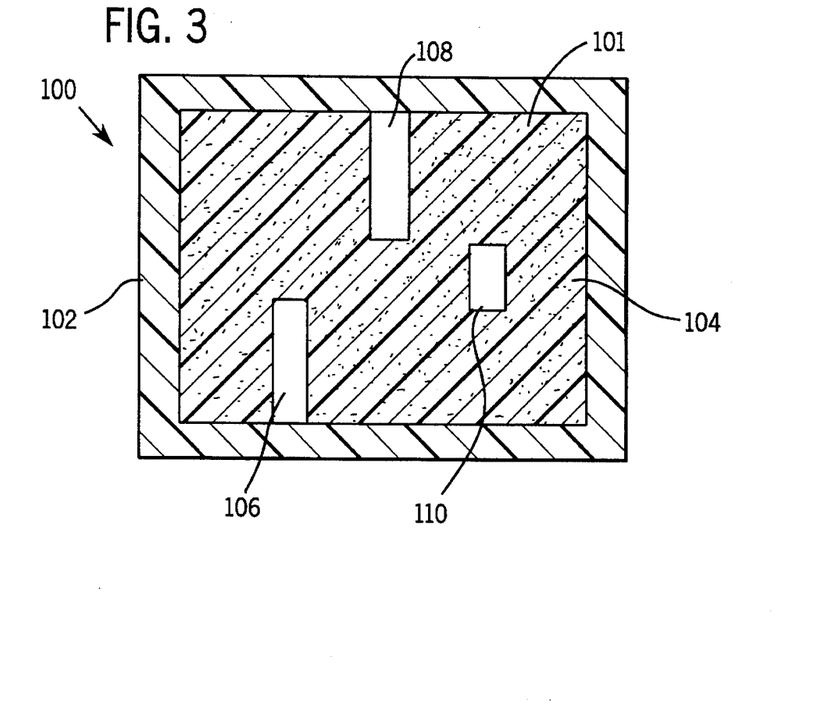
FIG. 3 is a sectional, side view of one preferred embodiment of the phantom containing a multi-sectioned well-shaped cyst.

Turning now to FIG. 3, a phantom 100 for use with the above described method is shown. In this preferred embodiment, an echogenic material 101 is surrounded by an enclosure 102. The enclosure 102 is sealed and contains a liquid 104. Enclosure 102 is preferably air-tight to prevent formation of bubbles within liquid 104. The presence of bubbles within liquid 104 is undesirable because the bubbles can create a significant degree of attenuation and scattering. Echogenic material 101 further defines sonolucent regions 106, 108, 110.

Echogenic material 101 can be any material which displays uniform scatter characteristics when imaged with an ultrasound device (not shown). Preferably, echogenic material 101 is a material that displays sonographic characteristics similar to the human body, such that the material is capable of approximating soft tissue with respect to (a) speed of sound, (b) attenuation coefficient, and (c) scattering coefficients. In one embodiment, echogenic material 101 is reticulated, open-cell polyurethane foam.

Liquid 104 is dispersed throughout echogenic material 101 and is utilized as a propagation medium for ultrasonic waves. In one embodiment, liquid 104 can be purified water. Additionally, other components such as alcohol, may be added to enhance ultrasonic wave propagation and/or inhibit growth of organisms that could cause wave attenuation or scatter.

Sonolucent regions 106, 108, 110 are hollow regions containing no echogenic material. When an ultrasonic wave enters these regions 106, 108, 110, the wave will pass through these regions without any back-scatter. In the preferred embodiment, three regions are shown, however, a different number of sonolucent regions can be present without departing from the spirit of the invention. Sonolucent regions 106, 108, 110 may also have various shapes, although it has been found that circular or square shaped wells work best with the above described method. Use of phantom 100 with the above described method has been found to be most beneficial when the center axes of sonolucent regions 106, 108, 110 are offset as is shown in FIG. 3. With offset axes, the effects of attenuation on the measurement are minimized.

Figure 4:
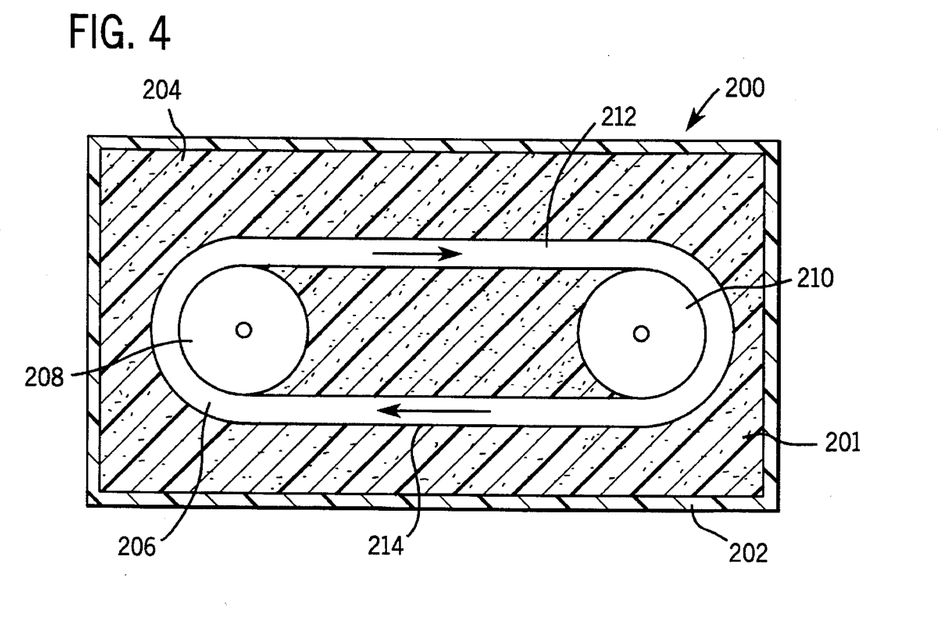
FIG. 4 is a sectional, side view of one preferred embodiment of the flow phantom having a rotating belt of a scattering density different than the surrounding matrix.

Turning now to FIG. 4, a preferred embodiment of flow phantom 200 is shown. In this preferred embodiment, echogenic material 201 having a first pore density is surrounded by an enclosure 202. Enclosure 202 is sealed and contains a liquid 204. Enclosure 202 is preferably air-tight to prevent formation of bubbles within liquid 204. Echogenic material 201 surrounds echogenic belt 206 which has a second pore density. Belt 206 rotates on pulleys 208, 210 such that when phantom 200 is imaged with an ultrasound device, belt 206 simulates blood flow. Pulleys 208, 210 can be driven by any standard drive means, such as an electric motor (not shown).

In the preferred embodiment, the first scatter density of material 201 is greater than the second scatter density of belt 206. This type of relationship most closely mimics the relationship between body tissues and blood because body tissue has greater scatter than blood. Furthermore, phantom 200 permits the measurement of motion at two different depths. When imaged from above, the upper portion 212 of belt 206 will appear to be a first blood vessel and the lower portion 214 of belt 206 will appear to be second blood vessel. Additionally, if the radii of pulleys 208, 210, are altered, the distance between these apparent blood vessels can be varied. Furthermore, the apparent diameter of these blood vessels can be varied by altering the thickness of belt 206.

In practice, it has been found that if the gain on the ultrasound system's monitor is adjusted down until reflections from belt 206 are not visible, the most satisfactory results are obtained. Specifically, when practiced in this manner, the scatter from belt 206 most closely resembles a fluid such as blood which is not visible in an ultrasound image, i.e., blood vessels should appear to be black or cystic.

Figure 5A:
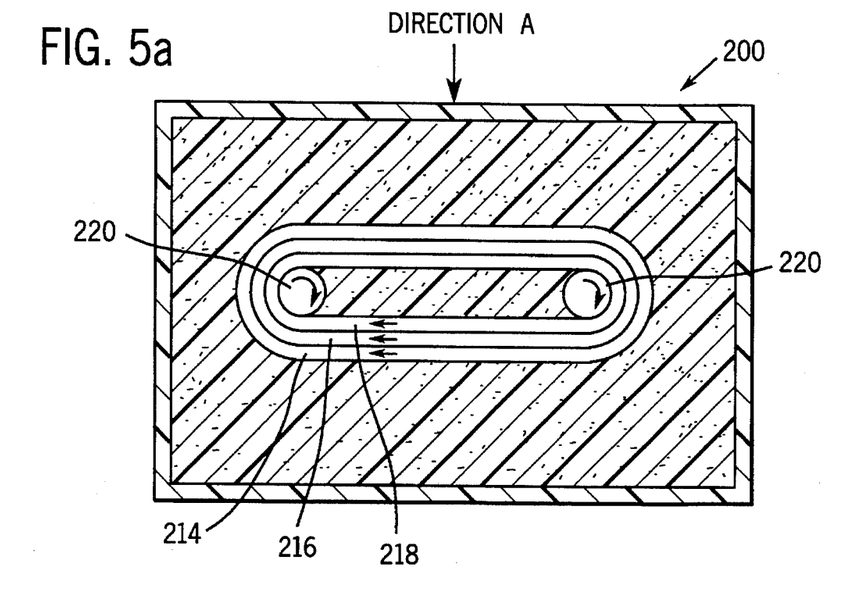
FIG. 5a is a sectional, side view of another preferred embodiment of the flow phantom wherein multiple belts of varying width are utilized.
Figure 5B:
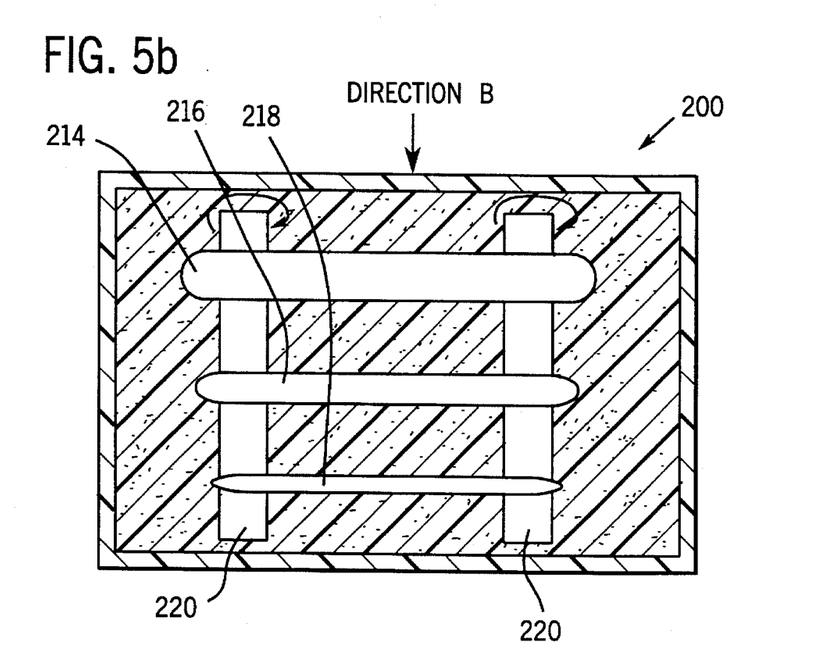
Figure 5C:
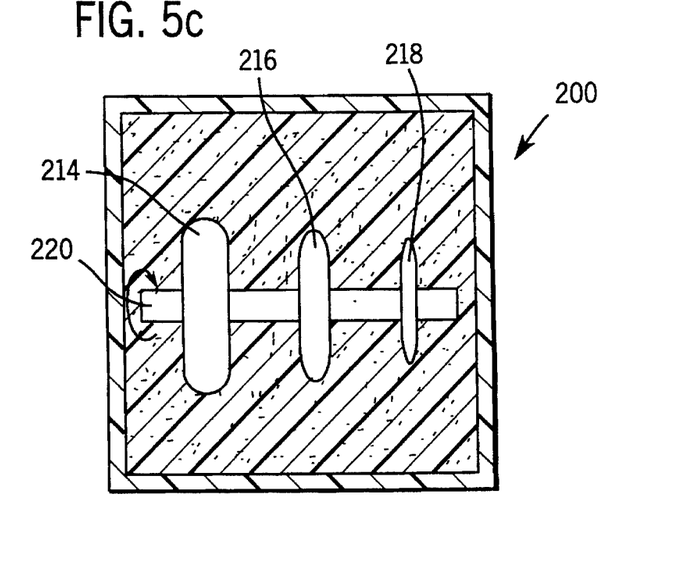

In another embodiment, illustrated in FIGS. 5a, 5b, 5c, phantom 200 is provided with multiple echogenic belts 214, 216, 218. These belts can be driven simultaneously by the same drive shaft 220. Belts 214, 216, 218 may vary in both thickness and width to simulate different diameter blood vessels. In the embodiment illustrated, belt 214 has a first thickness and a first width and belt 216 has a second thickness and a second width whose values are less than those of the first thickness and first width. Further, belt 218 has a third thickness and a third width whose values are less than those of the second thickness and second width. This variance between belt dimensions is necessary to optimize use of phantom 200. The smallest belt, belt 218, is incorporated to provide a echogenic region that is clinically difficult to image. This belt is useful in evaluating the sensitivity of the ultrasound system under investigation. On the other hand, mid-sized belt 216 is intended to provide an echogenic region which is easily imaged. Comparison of the images of belt 216 and belt 218 provides a qualitative evaluation of an ultrasound system's performance level. Further, largest belt 214 serves as a quantitative velocity calibration standard by providing such a large target area that the beam forming characteristics of the system are not a factor. Lastly, large belt 214 allows physical observation of the wall filter function, and provides a means to evaluate flow uniformity within a volumetric region.

If belts 214, 216, 218 are stationary, an ultrasound image of phantom 200 would reveal six cylindrical low scatter regions, i.e., cysts. These regions would appear as three different size cylinders at two different depths of interest.

Figure 6:
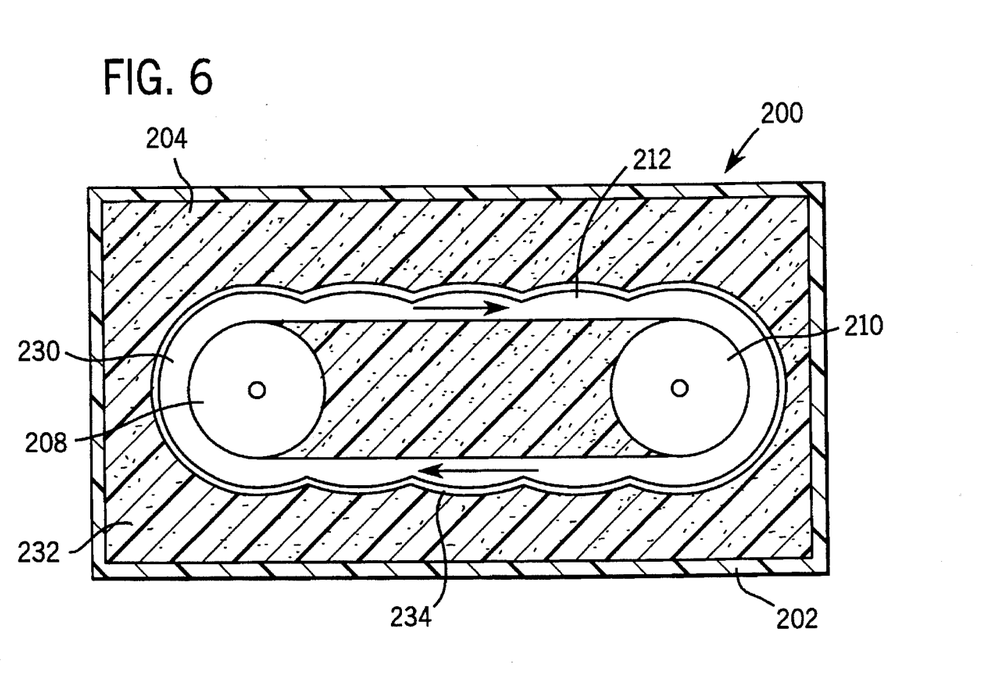
FIG. 6 is a sectional, side view of yet another preferred embodiment of the flow phantom wherein the belt is shaped to simulate systaltic movement.

FIG. 6 illustrates another embodiment of phantom 200. In this embodiment, echogenic belt 230 is provided with a shaped surface, and echogenic material 232 is biased against the surface of shaped belt 230. The shape of the surface of belt 230 can be provided simply by altering the thickness along the length of belt 230. One example of such a shape is the scalloped surface illustrated in FIG. 6. As shaped belt 230 rotates about pulleys 208, 210, the interface between echogenic material 232 and the shaped surface of belt 230 undulates. In other words, the biased echogenic material 232 is urged in and out by the forms carved into the surface of belt 230. A thin layer of a third echogenic material 234 may also be provided between echogenic material 232 and shaped belt 230. Preferably, third echogenic material 234 is selected to model the scatter characteristics of arterial vessel walls.

The effect of the above described undulation when imaged with an ultrasound system is that of systatic vessel movement. Specifically, the device as herein described models the systatic movement of blood vessels as the heart beats and, at the same time, mimics the flow of blood through those vessels. This embodiment is helpful in evaluating an ultrasound system's capability to reject vessel wall motion. Furthermore, the axial wall motion component directed toward the ultrasound device can be quantified and utilized, along with the geometric thickness variations and rotational speed of the belt, to design or evaluate wall motion filters.

Figure 7A:
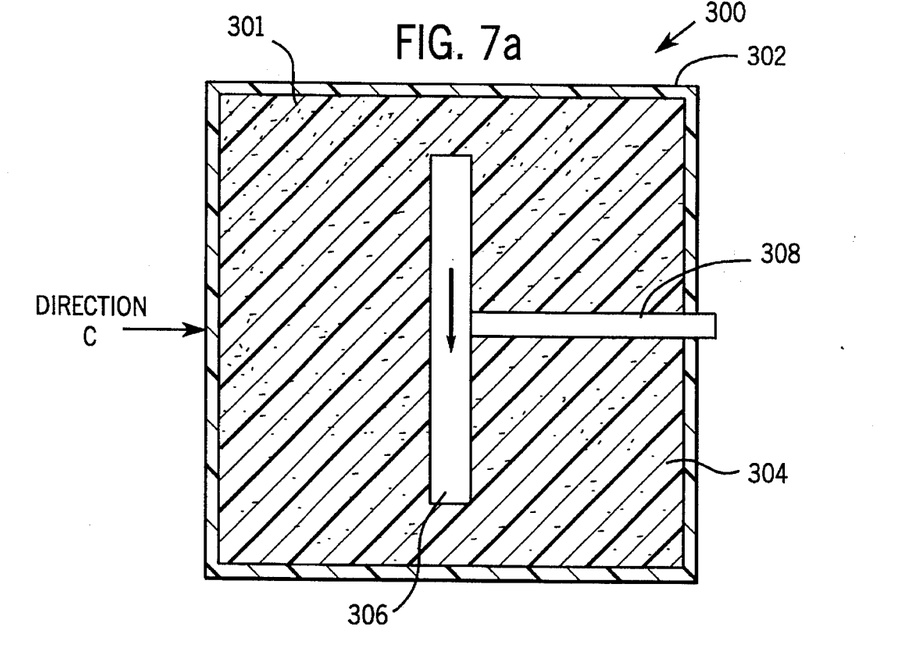
FIG. 7a is a sectional, top view of a fourth embodiment of the flow phantom wherein a rotating disk is used to mimic blood flow.
Figure 7B:
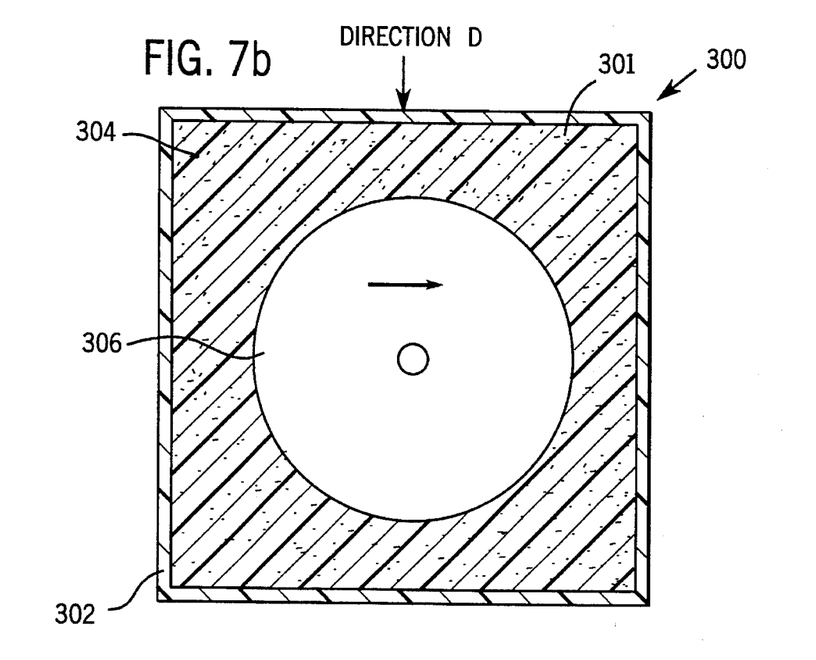

Still yet another embodiment of the flow phantom 300 is shown in FIGS. 7a and 7b. In this preferred embodiment, echogenic material 301 having a first scatter density is surrounded by an enclosure 302. Enclosure 302 is sealed and contains a liquid 304. Enclosure 302 is preferably air-tight to prevent formation of bubbles within liquid 304. Echogenic material 301 surrounds echogenic disk 306 which has a second pore density. Disk 306 rotates on shaft 308 which is driven by any standard drive means, such as an electric motor (not shown). When phantom 300 is imaged with an ultrasound device from Direction C, as is illustrated by FIG. 7a, disk 306 simulates blood flow. Alternatively, when phantom 300 is imaged from Direction D, the surface of disk 306 is imaged. In the preferred embodiment, the first scatter density of material 301 is greater than the second scatter density of disk 306. This type of relationship most closely mimics the relationship between body tissues and blood because body tissue has greater scatter characteristics than blood.

The preferred embodiment of phantom 300 offers several features not present in the preferred embodiment of the flow phantom which utilizes a belt. First, ease of construction is increased while cost of construction is decreased. Second, imaging the surface of disk 306, i.e., Direction C, provides an opportunity to evaluate the effects of spectral spreading on the ultrasound system. This evaluation is possible because the ultrasound beam is encountering different scatter velocities at different radial locations on rotating disk 306.

As is readily discernible from the drawings and description herein, the present invention discloses, in general terms, an ultrasound flow phantom having a movable first means for generating back-scatter from ultrasonic wave propagation passing through the phantom, and a second means for generating back-scatter from ultrasonic wave propagation also passing through the phantom. The second means for generating back-scatter comprises an echogenic material dispersed with a liquified material. The movable first means has wave propagation characteristics that are different than that of the second means when the first means is in motion, and the movable first means is disposed within the second means.

Although the invention has been described in considerable detail through the figures and above discussion, many variations and modifications can be made by one skilled in the art without departing from the spirit and scope of the invention as described in the following claims.

What is claimed is:

1. An ultrasound flow phantom comprising:
   a. at least one belt defined by a first section, a second section, a first end, a second end, an outer surface and an inner surface, said belt generating back-scatter from ultrasonic wave propagation passing through said belt; and
   b. a means for generating back-scatter from ultrasonic wave propagation in a manner different from the propagation effect by said belt, wherein said belt is disposed within the means for generating back-scatter, wherein said means for generating back-scatter comprises a solidified porous material dispersed with a liquified material.

2. The flow phantom of claim 1 further comprising:
   a. at least one first pulley; and
   b. at least one second pulley, wherein said belt is mounted on said first and second pulley such that said belt rotates in the direction of rotation of said first and second pulleys.

3. The flow phantom of claim 1 wherein said outer surface is flat.

4. The flow phantom of claim 1 wherein said outer surface is scalloped.

5. The flow phantom of claim 4 wherein said second means is biased against the outer surface of said belt.

6. The flow phantom of claim 4 further comprising an additional means for generating back-scatter from ultrasonic wave propagation, wherein said additional means is located between said means for generating back-scatter and the outer surface of said belt, such that said additional means is biased against the outer surface of said belt.

7. The phantom of claim 1 wherein said phantom is comprised of a first belt, a second belt and a third belt.

8. The phantom of claim 7 wherein the widths of said first, second and third belts differ.

9. The phantom of claim 7 wherein the thicknesses of said first, second and third belts differ.

10. The flow phantom of claim 7 wherein at least one outer surface of said first, second and third belts is scalloped.

11. The flow phantom of claim 10 wherein said means for generating back-scatter is biased against the outer surface of said first, second and third belts.

12. The flow phantom of claim 10 further comprising a third means for generating back-scatter from ultrasonic wave propagation, wherein said third means is located between said second means and the outer surfaces of said first, second and third belts, such that said third means is biased against the outer surfaces of said first, second and third belts.

13. An ultrasound flow phantom comprising:
   a. at least one rotatably mounted disk having a first surface and a second surface,
      wherein the at least one disk generating back-scatter from ultrasonic wave propagation therethrough; and
   b. a solidified porous material dispersed with a liquified material and located around said at least one disk for generating back-scatter from ultrasonic wave propagation in a manner different from that generated by said at least one disk.

14. The ultrasound flow phantom of claim 13 wherein at least one of said first and second surfaces is scalloped.

15. The flow phantom of claim 14 further comprising an additional means for generating back-scatter from ultrasonic wave propagation, wherein said additional means is located around said at least one disk, such that said additional means is biased against the first and second surfaces of said at least one disk.

16. An ultrasound flow phantom comprising:
   a. a movable first means for generating back-scatter from ultrasonic wave propagation passing through the phantom; and
   b. a second means for generating back-scatter from ultrasonic wave propagation passing through the phantom, wherein the second means comprises a solidified porous material dispersed with a liquified material, the movable first means having wave propagation characteristics different than that of the second means when the first means is in motion, and wherein the movable first means is disposed within said second means.

17. The ultrasound flow phantom of claim 16 wherein the solidified porous material of the second means is foam.

18. The ultrasound flow phantom of claim 16 wherein the solidified porous material of the second means is reticulated, open-cell polyurethane foam.

19. The ultrasound flow phantom of claim 16 wherein the liquified material has ultrasonic propagation characteristics similar to that of human body tissue.

20. The ultrasound flow phantom of claim 16 further comprising a sealed enclosure wherein the second means occupies a substantial portion of the sealed enclosure, and the first means occupies the remaining portion of the sealed enclosure.

21. An ultrasound flow phantom comprising:

at least one belt defined by a first section, a second section, a first end, a second end, a scalloped outer surface, and an inner surface, said belt further comprising a first means for generating back-scatter from ultrasonic wave propagation passing through said belt; and a second means for generating back-scatter from ultrasonic wave propagation in a manner different from the alteration effect by said first means, wherein said second means is located around said belt and interposed between the first and second sections of said belt.

22. The flow phantom of claim 21 wherein said second means is biased against the outer surface of said belt.

23. The flow phantom of claim 21 further comprising a third means for generating back-scatter from ultrasonic wave propagation, wherein said third means is located between said second means and the outer surface of said belt, such that said third means is biased against the outer surface of said belt.

24. The ultrasound flow phantom of claim 21 comprising a first belt, a second belt, and a third belt, wherein at least one outer surface of each belt is scalloped.

25. The flow phantom of claim 24 wherein said second means is biased against the outer surface of said first, second and third belts.

26. The flow phantom of claim 21 further comprising a third means for generating back-scatter from ultrasonic wave propagation, wherein said third means is located between said second means and the outer surfaces of said first, second and third belts, such that said third means is biased against the outer surfaces of said first, second and third belts.

* * * * *

UNITED STATES PATENT AND TRADEMARK OFFICE
CERTIFICATE OF CORRECTION

PATENT NO. : 5,560,242

DATED : October 1, 1996

INVENTOR(S) : Flax, Stephen J.

It is certified that error appears in the above-indentified patent and that said Letters Patent is hereby corrected as shown below:

Column 12:

Claim 12, line 2, delete "a third" and substitute therefor -- an additional --;

Claim 12, line 3, delete "third" and substitute therefor -- additional --;

Claim 12, line 4, delete "second";

Claim 12, line 4, after "means" insert -- for generating back-scatter --;

Claim 12, line 5, delete the second occurrence of "third", and substitute therefor -- additional --.

Signed and Sealed this

Third Day of June, 1997

Attest:

BRUCE LEHMAN

Attesting Officer

Commissioner of Patents and Trademarks